(12) United States Patent
Bovenberg et al.

(10) Patent No.: US 7,402,383 B2
(45) Date of Patent: Jul. 22, 2008

(54) PROCESS FOR PREPARING VARIANT POLYNUCLEOTIDES

(75) Inventors: Roelof Ary Lans Bovenberg, DA Rotterdam (NL); Richard Kerkman, NL Zandvoort (NL)

(73) Assignee: DSM IP Assets B.V., TE Heerlen (NL)

( * ) Notice: Subject to any disclaimer, the term of this patent is extended or adjusted under 35 U.S.C. 154(b) by 113 days.

(21) Appl. No.: 10/484,682

(22) PCT Filed: Jul. 23, 2002

(86) PCT No.: PCT/EP02/08225

§ 371 (c)(1),
(2), (4) Date: Jan. 23, 2004

(87) PCT Pub. No.: WO03/010183

PCT Pub. Date: Feb. 6, 2003

(65) Prior Publication Data

US 2005/0130141 A1    Jun. 16, 2005

(30) Foreign Application Priority Data

Jul. 23, 2001  (EP) ................................. 01202821
Sep. 11, 2001  (EP) ................................. 01203457

(51) Int. Cl.
*C12Q 1/68* (2006.01)
*C12P 19/34* (2006.01)

(52) U.S. Cl. .......................... 435/6; 435/91.2

(58) Field of Classification Search ....................... None
See application file for complete search history.

(56) References Cited

U.S. PATENT DOCUMENTS

| | | | |
|---|---|---|---|
| 6,153,410 A * | 11/2000 | Arnold et al. ............... | 435/91.2 |
| 6,159,690 A | 12/2000 | Borrebaeck et al. ............ | 435/6 |
| 6,242,222 B1 * | 6/2001 | Gifford ........................ | 435/91.2 |
| 6,767,701 B1 * | 7/2004 | Vind ............................ | 435/6 |
| 2005/0130140 A1 | 6/2005 | Bovenberg et al. | |
| 2005/0130141 A1 | 6/2005 | Bovenberg et al. | |

FOREIGN PATENT DOCUMENTS

| EP | 1 108 783 | 6/2001 |
|---|---|---|
| WO | WO95/22625 | 8/1995 |
| WO | WO97/07205 | 2/1997 |
| WO | WO98/01581 | 1/1998 |
| WO | WO98/31837 | 7/1998 |
| WO | WO-98/41623 | 9/1998 |
| WO | WO01/29212 | 4/2001 |

OTHER PUBLICATIONS

Hemsley et al. ("A simple method for site-directed mutagenesis using the polymerase chain reaction" Nucleic Acids Research. 1989. vol. 17, No. 16: pp. 6545-6551).*
Zhou et al. ("Random mutagenesis of gene-sized DNA molecules by use of PCR with Taq polymerase" Nucleic Acid Research. 1991. vol. 19, No. 21: p. 6052).*
Ho et al. ("Site-directed mutagenesis by overlap extension using the polymerase chain reaction" Gene. Apr. 15, 1989;77(1):51-9).*
Horton et al. "Engineering hybrid genes without the use of restriction enzymes: gene splicing by overlap extension" Gene. Apr. 15, 1989;77(1):61-8.*
Coco et al., Nature Biotechnology (2001) 19(4):354-359.
Gibbs et al., Gene, Elsevier Biomedical Press (2001) 271(1):13-20.
Kikuchi et al., Gene, Elsevier Biomedical Press (2000) 243(1-2):133-137.
Volkov et al., Nucleic Acids Research, Oxford University Press (1999) 27(18):e18.
Fromant et al., Analytical Biochemistry (1995) 224:347-353.
Ge and Rudolph, BioTechniques (1997) 22:28-30.
Higuchi et al., Nucleic Acids Research (1988) 16(15):7351-7367.
Horton et al., Gene (1989) 77:61-68.
Ho et al., Gene (1989) 77:51-59.
Landt et al., Gene (1990) 96:125-128.
Li and Shapiro, Nucleic Acids Research (1993) 21(16):3745-3748.
Picard et al., Nucleic Acids Research (1994) 22(13):2587-2591.
Sambrook and Russell, Molecular Cloning: A Laboratory Manual, Third Edition, vol. 2, Cold Spring Harbor Laboratory Press, New York (2001) pp. 13.36-13.39 and 13.79-13.80.

* cited by examiner

*Primary Examiner*—Kenneth R. Horlick
*Assistant Examiner*—Christopher M. Babic
(74) *Attorney, Agent, or Firm*—Nixon & Vanderhye P.C.

(57) ABSTRACT

The present invention discloses a process for the preparation of variant polynucleotides using a combination of mutagenesis of a starting population of polynucleotides and recombination of the mutated polynucleotides. The process comprises the steps of subjecting a population of polynucleotides to (a series of) two (or more) separate PCR's comprising a first PCR with a forward mutation-specific primer for a position to be mutated and a reverse universal primer and a second PCR with a forward universal primer and a reverse mutation-specific primer for a position to be mutated. The products of the (series of) two (or more) PCR's are assembled by a polymerase, preferably in one tube.

13 Claims, 2 Drawing Sheets

PROCESS FOR PREPARING VARIANT POLYNUCLEOTIDES

BACKGROUND OF THE INVENTION

CROSS-REFERENCE TO RELATED APPLICATION

This application is the national phase of PCT application PCT/EP 02/08225 having an international filing date of 23 Jul. 2002, which claims priority from European applications Nr. 01203457.5, filed 11 Sep. 2001 and Nr. 01202821.3, filed 23 Jul. 2001. The contents of these documents are incorporated herein by reference.

Protein engineering technology includes the creation of novel proteins by targeted modificaton(s) of known proteins. However, an approach directed to targeted modification is only applicable to proteins or protein families of which the three-dimensional structure of the protein or at least one member protein of the family has been resolved. Furthermore, many attempts to alter the properties of enzymes by this approach have failed because unexpected changes in the structure were introduced. If random mutagenesis is applied to create modified proteins, it appeared that successfully modified proteins often possessed amino acid substitutions in regions that protein modeling could not predict.

Various approaches have been developed to mimic and accelerate nature's recombination strategy to direct the evolution of proteins to more beneficial molecules. Direct evolution is a general term used for methods for random in vitro or in vivo homologous recombination of pools of homologous polynucleotides. Several formats are described, for instance random fragmentation followed by polymerase-assisted reassembly (WO9522625), in vivo recombination (WO97/07205, WO98/31837) or staggered extension of a population of polynucleotide templates (WO97/07205, WO98/01581). In this way an accumulation of beneficial mutations in one molecule may be accomplished.

The method of the present invention advantageously enables the mutagenesis of a polynucleotide and the random combination of mutated positions to be performed in one process, without the necessity for prior fragmentation of the polynucleotide. The method is reproducible, highly controllable and very fast. A further advantage of the method of the invention is that the recombination frequency is high and the chance to re-isolate the starting polynucleotide is low.

DETAILED DESCRIPTION

The present invention provides a method for the preparation of a variant polynucleotide.

The method according to the invention comprises the steps of:
subjecting a population of polynucleotides to two or more separate PCR's, a first PCR with a forward mutation-specific primer directed to a position to be mutated and a reverse universal primer, a second PCR with a forward universal primer and a reverse mutation-specific primer directed to a position to be mutated, and, optionally, a third or
more PCR with a suitable forward and reverse primer;
assembling the products of the two or more PCR's by a polymerase;
optionally amplifying the assembled polynucleotides;
preparing a library of the resulting variant polynucleotides;
screening said library of variant polynucleotides for a variant polynucleotide with a desired property.

A variant polynucleotide is defined herein as a polynucleotide differing in at least one position from any one of the members of the population of polynucleotides that forms the starting material for the process according to the invention.

The population of polynucleotides that forms the starting material for the process according to the invention comprises polynucleotide members that display a substantial homology to each other. A substantial homology is defined herein as a homology from 70-100%, preferably from 75-100%, preferably from 80-100%, preferably from 85-100%, more preferably from 90-100%, most preferably from 95-100%. A population of polynucleotides comprising polynucleotide members displaying a substantial homology for instance may be a population of polynucleotides wherein the polynucleotide members are identical polynucleotides, and/or are mutants of a parental polynucleotide and/or are members of a gene family.

A population of identical polynucleotides may for instance be a population of polynucleotides encoding a wild type polypeptide.

A population of mutants derived from a parental polynucleotide may comprise different mutants, each individual mutant in the population differing in at least one position from the parental polynucleotide. A population of different mutants derived from a parental polynucleotide may be obtained by methods known in the art. For instance, the mutants may be obtained by classical random or site-directed mutagenesis techniques. A suitable random mutagenesis technique for Instance is the error-prone PCR technique.

The population of mutants may comprise mutants that have been previously screened and selected for a certain desired property.

A population of members of a gene family typically contains different members of a gene family, i.e. polynucleotides displaying a considerable sequence homology, i.e. at least 70%, and having a similar function in an organism. For instance, such polynucleotides may encode related proteins originating from different strains, different species, different genera, different families. An example is the phytase gene family from the genus *Aspergillus*, displaying a homology of at least 90% within the species *Aspergillus niger*.

The starting population of polynucleotides may conveniently be subjected to the process of the invention when being cloned in a vector and/or as isolated fragments. In a situation that the starting population of polynucleotides is obtained by a prior screening and selection process, the vector may conveniently be an expression vector.

According to the method of the invention, the starting population of polynucleotides is subjected to two or more separate polymerase chain reactions (PCR's), a first PCR with a forward mutation-specific primer for a position to be mutated and a reverse universal primer, a second PCR with a forward universal primer and a reverse mutation-specific primer for a position to be mutated, and, optionally, a third or more PCR with a suitable forward and reverse primer.

The first PCR generates fragments with a common 3' end and different 5' ends, the 5' end being determined by the position of the forward mutation-specific primer within the starting polynucleotide sequence. The second PCR generates fragments with a common 5' end and different 3' ends, the 3' end being determined by the position of the reverse mutation-specific primer within the starting polynucleotide sequence.

The third or more PCR may generate fragments that, for instance, are positioned in between the fragments obtained in the first and second PCR. A third or more PCR may be applied, for instance, if the starting population of polynucleotides comprises members which size is such that the application of two PCR's will result in an inconveniently low yield of full-length assembled product after the assembly (fusion) PCR. Suitable forward and reverse primers for the third or more PCR are chosen such that the resulting PCR product(s) will overlap with the adjacent 5' and 3' fragments. The primers suitable for the third or more PCR may contain a mutated position.

Preferably, any forward mutation-specific primer has a corresponding reverse mutation-specific primer, i.e. sets of mutation-specific forward and reverse primers are designed directed to the same nucleotide position(s) within a polynucleotide member of the starting population of polynucleotides.

Preferably, a series of two or more separate PCR's is performed using one set of forward and corresponding reverse mutation-specific primer per separate PCR, resulting in a series of separate PCR products.

The mutation-specific primer is designed in such a way that at least one nucleotde position within the primer differs from the corresponding nucleotide position within a member of the starting population of polynucleotides. This (these) position(s) is (are) called the mutated position(s). Typically, the mutated position(s) within the primer is (are) located at least one nucleotide from the end of the primer. The number of mutated positions per primer and the length of the primer are not critical to the invention and may conveniently be determined on a case by case basis. The number of mutated positions per primer for instance may depend on the length of the primer, whereas the length of the primer may depend on the type of primer used (e.g. saturated or spiked).

In one embodiment of the invention, a (series on mutation-specific primer(s) is designed in such a way that a mutated position in a primer corresponds to a selected position, e.g. a position that is shown to be an effective mutation, in a member of the starting population of polynucleotides.

In another embodiment of the invention, a (series of) mutation-specific primer(s) is designed in such a way that the primer(s) ensure the introduction of mutations at random positions within the starting population of polynucleotides.

In still another embodiment of the invention, the mutation-specific primer is a saturated primer, i.e. a primer designed to introduce altered nucleotides in a triplet encoding an amino acid such that more than one amino acid substitution is introduced at a particular position in the polypeptide encoded by the polynucleotide to be modified. Preferably, the saturated primer is designed such that a substitution is possible of an amino acid of choice with any of the other 19 amino acids naturally occurring in a protein. A saturated primer typically has a length of about 18-30 nucleotides. A saturated primer effectively comprises a mixture of individual oligonucleotides wherein any individual oligonucleotide enables substitution of a chosen amino acid for any one of the other amino acids.

In still another embodiment of the invention, the mutation specific primer is a spiked primer (or spiked oligonucleotide). A spiked oligonucleotide contains, per nucleotide to be mutated, for instance a nucleotide within a codon, a majority of the original nucleotide and a minority of the nucleotide to be substituted. A suitable percentage for the majority of the original nucleotide is 80-99%. The length of a spiked oligonucleotide may depend on the length of the polynucleotide to be mutated and/or the number of desired mutations. It is convenient that at the ends of a spiked oligonucleotide, at least two nucleotides will be 100% similar to the original nucleotide sequence, i.e. will not be mutated.

For instance, an oligonucleotide of 55 nucleotides containing 5 nucleotides at both ends that are not mutated and being spiked with a percentage of 4.5% over the remaining 45 nucleotides will yield about two substitutions per oligonucleotide.

Of course, the skilled person is very well able to combine any of the embodiments mentioned above if desired.

The universal primers used in the process of the invention may be directed to the vector and/or to the polynucleotide to be used. Preferably, the universal primers contain a unique restriction enzyme site enabling the cloning of the resulting variant polynucleotides in a suitable vector.

According to the invention, the products of the two or more separate PCR's are mixed, preferably in equimolar amounts, and assembled by a polymerase, in a so-called assembly or fusion PCR. Optionally, additional universal forward and reverse primer may be added to the assembly reaction mixture to simultaneously amplify the assembled polynucleotides by PCR.

In one embodiment of the invention, the series of separate PCR products obtained from a series of two or more separate PCR's are assembled by a polymerase in one tube, in other words subjected to a one-tube fusion PCR. Preferably, the separate PCR products are mixed in equimolar amounts.

In another embodiment of the invention, the series of separate PCR products obtained from a series of two or more separate PCR's are separately assembled by a polymerase, in other words subjected to separate fusion PCR's. A separate fusion PCR's is performed with the products of the first, second and optionally third PCR. This embodiment may be advantageous if a set of forward and reverse mutation-specific primer contains two or more mutations per primer.

In a situation that mutations are desired only near the end(s) of a polynucleotide, it may be an option to apply one PCR that effectively combines the two or more separate PCR's and the fusion PCR in one reaction.

The method of the invention advantageously enables the mutagenesis of a polynucleotide and the random combination of mutated positions in one process. In addition, the present invention advantageously enables the option to isolate "intermediate" variant polynucleotide products by subjecting the products of any desired set of forward and reverse mutation-specific primer to separate fusion PCR's. (Selected) variant polynucleotide resulting from several separate PCR's according to the invention can then be used as starting material for a further PCR according to the invention.

Any of the PCR's as performed in the method of the invention may be performed following conditions generally known to the person skilled in the art. The conditions typically may depend on the primers and the enzyme used. It may further be an option to perform any of said PCR's under error-prone conditions, i.e. under conditions that reduce the fidelity of nucleotide incorporation, thus randomly introducing additional mutations in the variant polynucleotides obtained by the method of the invention. Error-prone conditions may for instance be provided by independently varying the concentrations of manganese and dGTP in the PCR reaction. Typically, the mutagenesis rate may be raised by increasing the amount of manganese and/or dGTP in the PCR reaction.

The polynucleotide products of the assembly reaction are cloned in a suitable vector, to enable the preparation of a library of variant polynucleotides. The choice of the vector will depend on the host wherein the library is propagated. Subsequently, the library of variant polynucleotides is screened with a suitable screening method to enable the selection of a variant polynucleotide with a desired property.

The method used for screening the library of variant polynucleotides is not critical for the invention. Typically, the method used will depend on a property of the polynucleotide of interest. If the polynucleotide of interest comprises a gene encoding a polypeptide, a suitable screening method may be directed to directly assay said polypeptide. A suitable screening method may further be directed to assay a primary or secondary metabolite if the polypeptide is an enzyme involved in the production of said primary or secondary metabolite, for instance an enzyme that is part of the biosynthetic pathway of said metabolite. Examples of such metabolites are an amino acid, a vitamin, an antibiotic, a carotenoid.

The method of the invention is suitable for the mutagenesis of any polynucleobde of interest.

In one embodiment of the invention, the polynucleotde of interest comprises a gene encoding a polypeptide. Said polypeptide may for instance be a structural protein, a peptide hormone, a growth factor, an antibody or an enzyme. The polypeptide may be produced intracellularly or may be secreted from the cell into the environment, for instance the culture medium. The polynucleotide may comprise a single gene or may comprise a cluster of genes. Said cluster of genes may comprise genes encoding enzymes involved in the biosynthesis of a particular metabolite and/or genes encoding regulatory factors involved in the regulation of expression of one or more genes involved in production of a particular metabolite.

In another embodiment of the invention, the polynucleofide of interest may be a non-coding polynucleotide, for instance a regulatory region involved in the control of gene expression, on transcriptional and/or translational level. The process of the invention may also be applied to a polynucleobde comprising a gene (cluster) and corresponding regulatory regions.

The present invention further envisages production of a variant polypeptde by expressing a variant polynucleotide produced and selected according to the invention in a suitable host organism and, optionally, recovery of the produced polypeptide.

To this end, the selected polynucleotide is cloned in an expression vector of choice and transformed to a host organism of choice. Transformed host cells are selected from the untransformed background by any suitable means. The transformed cells are grown in a suitable culture medium and may further be screened for expression of the variant polynucleotide. Techniques for the transformation of host cells and for the selection of transformed cells are commonly known to the skilled person.

For production of the variant polypeptide on a larger scale, a transformed cell producing a suitable amount of the variant polypeptide of interest may be cultured under conditions conducive to the production of said polypeptide. Optionally, the polypeptide may be recovered from the culture medium and/or form the host organism. Depending on its further use, recovery of the variant polypeptide may include its formulation in a suitable liquid or solid formulation, and/or its immobilization.

Above 1-9: DNA product after a PCR reaction with the universal 5' primer and mutation primers 1-9.

Under 1'-9': DNA product after a PCR reaction with the universal 3' primer and mutation primers 1'-9'.

Figure 3:
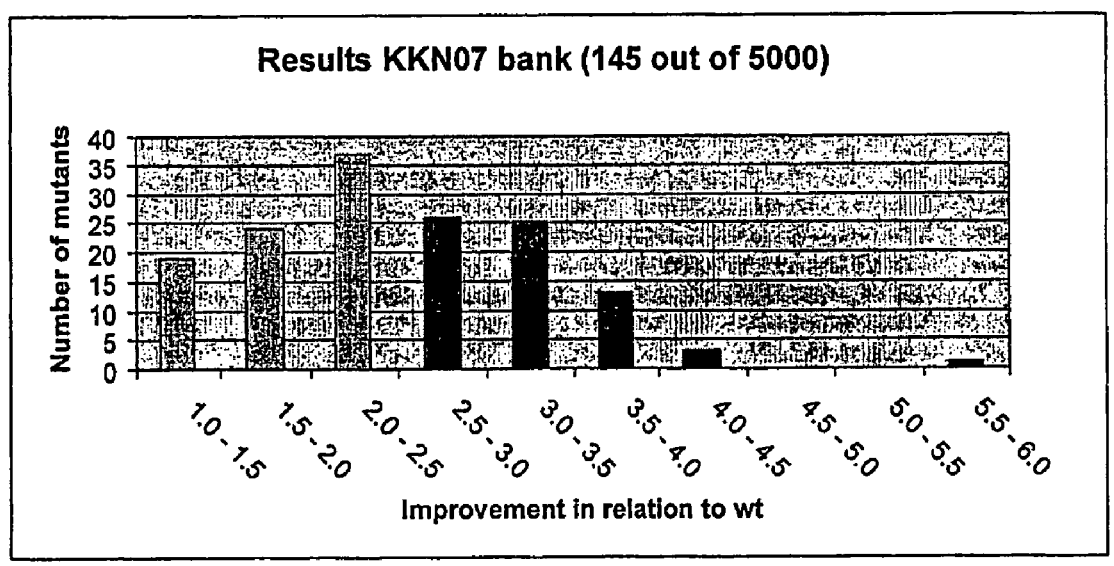

FIG. 3. Typical results of the conversion activities of a group of mutants from part of the KKN07 library selected after the first MTP analysis.

EXPERIMENTAL

MTP Screening

Single colonies of the library to be screened were inoculated in individual wells of microtiter plates (MTP's) filled with SE liquid medium (containing bacto tryptone 10 g/l, bacto yeast 5 g/l and NaCl 5 g/l), supplemented with ampicillin at a final concentration of 100 μg/ml. If required, arabinose inducer was added (final concentration 0.002%). Normal growth conditions were at 37° C.; induced growth conditions were at 28° C. and 280 rpm. 50 μl of the 20-24 hour grown cultures were incubated with D,L-α-methylphenylglycine amide (Femam) at 55° C. in deepwell plates. After 2.5 hours off incubation the amidase activity of the culture broth was measured by measuring the amount of formed L-α-methylglycine (Femac).

CFE Screening

Cell-free extracts (CFE's) were prepared using a bacterial protein extraction reagent according to the manufacturers instructions (BPER, Pierce, Rockford, Ill. USA) and their L-amidase activity was measured.

Amidase Activity Assay

Amidase activity was measured as conversion activity from Femam to Femac. Detection occurred by NMR.

Example 1

Preparation and Screening of an Error-prone Library of *O. anthropi* L-amidase

An error-prone PCR was performed on the *Ochrobactrum anthropi* L-amidase gene (see SEQ ID No 1) using the Diversify™ PCR Random Mutagenesis kit from Clontech (Palo Alto, Calif. USA) according to the manufacturer's instructions. The PCR products were cloned In the Eagl/HindIII sites of the vector pBAD/Myc-HisC (Invitrogen Corporation, Carlsbad, Calif. USA) and transformed to *E. coli* Top10F cells (Invitrogen Corporation, Carlsbad, Calif. USA). Clones were first screened on MTP and CFE's of a subset of clones were further screened (see Experimental). Improved mutants were sequenced to determine the modified position(s). The modified positions of seven improved mutants are indicated hereinafter V52A, F93V, T143A, T193P, N212D, N98I/L124P, K13BR/G234V (see SEQ ID No 2).

Example 2

Mutagenesis and Recombination of Improved Mutants by Mutation Primer PCR

Figure 1:
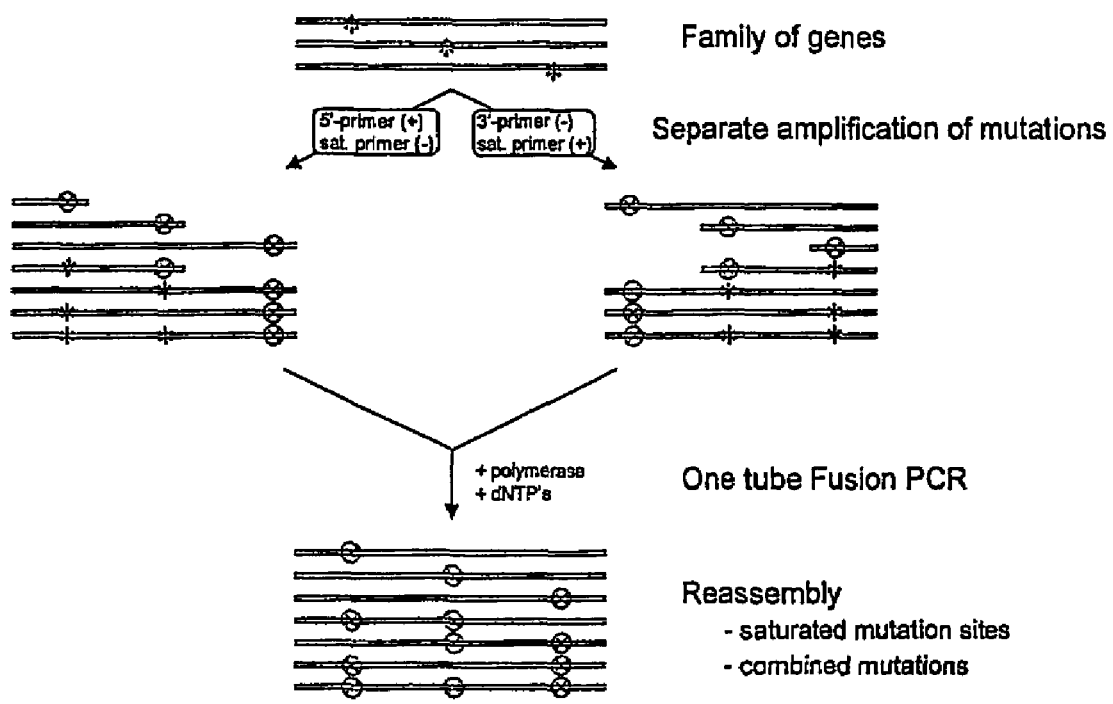
FIG. 1. Schematic illustration of (saturated) Mutation Primer PCR DNA Recombination. * mutated position; ⓧ saturated mutation site FIG. 2. Agarose gel electrophoresis of the single step PCR's.

Saturation mutagenesis at sites discovered after screening error-prone mutagenesis libraries will introduce all 20 amino acids into these positions. Saturated forward and reverse primers were designed for each mutation of the seven improved mutants obtained in Example 1. The saturated primers are designed with three N's at the codon of the amino acid to be mutated As can be seen in FIG. 1 two separate PCR reactions for each mutation site were performed 1) using a forward saturated primer in combination with a universal reverse primer, and 2) the reverse saturated primer in combination with a universal forward primer.

Figure 2:
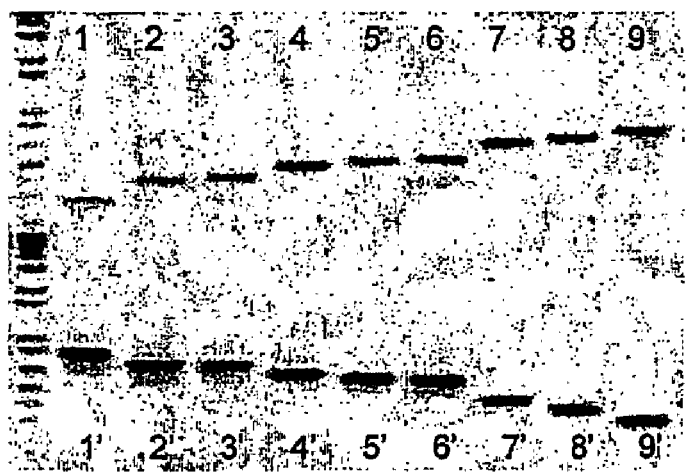

The PCR products of these separate PCR reactions (see FIG. 2) were mixed in equimolar amounts and assembled by polymerase. The products of this so-called fusion PCR reaction were subsequently amplified in an error-prone PCR. The DNA products were cloned in the EagI/HindIII sites of the pBAD/Myc-HisC vector and transformed to E. coli Top10F cells.

5000 clones of the resulting KKN07 library were screened in MTP. Approximately 40% of all the mutants analyzed proved to be inactive in MTP.

A large group of mutants selected from the MTP screening was tested in a secondary screening. In this screening, CVE's and different dilutions thereof were analysed for conversion activity by NMR. The conversion/µl was calculated and corrected for the amount of protein. Subsequently the conversion/µl/mg protein of the mutants was compared with conversion/µl/mg protein of the wild type, and the activity improvement was determined.

In FIG. 3 the overall results of selected mutants from the KKN07 library are presented. DNA of 10 randomly picked mutants and the 10 most improved mutants was sequenced.

The results of these sequence analyses are presented in Table 1.

From the sequence results of the randomly picked mutants a recombination frequency of about 70% was calculated (3 triple, 4 double and 3 single mutations). The mutation rate of the used error-prone conditions was approximately 0.9 mutations/gene.

Using one cycle of mutagenesis by error-prone PCR, saturation mutagenesis combined with recombination and screening/selection of a fraction of the library, the specific activity of *Ochrobactrum anthropi* L-amidase towards Femam was improved by approximately 5-6 times as compared to wild type

TABLE 1

Sequence results of 10 randomly picked mutants (KKN07-1/10) as well as 10 of the most improved mutants from the KKN07 library. At the top of the table the 7 selected mutants that were used as starting material are indicated. The conversion activity is indicated relative to wild type.

| | Mutations | | | | | | | | EP Mutations | | Conversion activity |
|---|---|---|---|---|---|---|---|---|---|---|---|
| WT | | | | | | | | | | | 1 |
| T1 | | | | | | T143A | | | | | 1.8-2.3 |
| T8 | | F93V | | | | | | | | | 1.5 |
| F10 | | | N98I | L124P | | | | | | | 1.4 |
| F162 | | | | | K138R | | | | G234V | | 1.3 |
| F190 | | | | | | | | N212D | | | 1.1 |
| R9 | | | | | | | T193P | | | | 1.4 |
| R10 | V52A | | | | | | | | | | 2.0-2.5 |
| KKN07-1 | V52A | | | | K138R | | | N212C | T123R, T273A | | |
| KKN07-2 | | F93T | | | | | | | R132C, Deletion | | |
| KKN07-3 | V52W | | N98E | | | T143A | | | | | |
| KKN07-4 | | | | L124T | | | T193P | | | | |
| KKN07-5 | V52A | | | | | T143K | | N212D | | | |
| KKN07-6 | V52T | | | | | | | | Deletion | | |
| KKN07-7 | | | | | | T143A | | | C285Y | | |
| KKN07-8 | | | | | | T143K | | N212D | | | |
| KKN07-9 | | | | | K138* | T143L | | | D222N | | |
| KKN07-10 | V52A | | | | | | | | G234V | F306S, A281T | |
| F308 | V52A | | | | | T143A | T193P | | G234C | R229W | 5.6 |
| F317 | | | N98I | L124G | | | T193P | | | | 4.5 |
| F303 | V52A | | | | | T143E | | | | | 4.5 |
| F386 | | | N98L | | K138R | | T193P | | | R132C | 4.3 |
| F409 | V52A | | | | | T143A | | | G234Q | L240F | 4.1 |
| F382 | V52A | | | | K138R | | T193P | | | P224T | 4 |
| F384 | | F93V | | | | | T193P | | | A116T | 3.7 |
| F389 | V52S | | | | | | T193P | | | | 3.6 |
| F302 | V52S | | N98V | | | T143A | | | | | 3.7 |
| F401 | | | | | | | T193P | N212T | | | 3.6 |

*stands for stop codon

The invention of claim:

1. A process for preparing a population of variant polynucleotides comprising at least one polynucleotide having a desired property, comprising:
   (a) subjecting a starting population of polynucleotides comprising at least two different mutants of a parental polynucleotide to separate PCR's to result in products of the PCR's, wherein the at least two different mutants were selected for the desired property:
      (i) a first set of at least two PCR's, which are performed separately from each other, with each PCR using a forward mutation-specific primer which hybridizes to a mutated position in a mutant of the starting population and a reverse universal primer to generate a first common end for the first set of PCR's,
      (ii) a second set of at least two PCR's, which are performed separately from each other, with each PCR using a forward universal primer to generate a second common end for the second set of PCR's and a reverse mutation-specific primer which hybridizes to a mutated position in a mutant of the starting population, and
      (iii) optionally a third or more PCR with suitable forward and reverse primers;
   (b) assembling the resulting products of the PCR's using a polymerase to obtain said population of variant polynucleotides, wherein the variant polynucleotides differ in at least one position from the parental polynucleotide; and
   (c) optionally amplifying the population of variant polynucleotides.

2. The process of claim 1, wherein the starting population of polynucleotides displays homology within said population of 70-100%.

3. The process of claim 1, wherein at least one mutation-specific primer is a saturated primer.

4. The process of claim 1, wherein at least one mutation-specific primer is a spiked oligonucleotide.

5. The process of claim 1, wherein the PCR's and/or the amplification of assembled polynucleotides are performed under error-prone conditions.

6. The process of claim 1, wherein the at least one variant polynucleotide having a desired property comprises one or more gene(s) encoding a polypeptide.

7. The process of claim 1, wherein the at least one variant polynucleotide encodes an enzyme involved in biosynthesis of a primary or secondary metabolite.

8. A process for producing a variant polypeptide comprising expressing the at least one variant polynucleotide prepared according to the process of claim 1 in a suitable host and, optionally, recovering the variant polypeptide.

9. A process for producing a primary or secondary metabolite comprising expressing the at least one variant polynucleotide prepared according to the process of claim 7 in a suitable host and, optionally, recovering the primary or secondary metabolite.

10. The process of claim 1 which further comprises:
    (d) preparing a library of said variant polynucleotides and
    (e) screening the library for said at least one variant polynucleotide with a desired property.

11. The process of claim 1, wherein the at least one polynucleotide encodes an enzyme.

12. A process for preparing a population of variant polynucleotides comprising at least one polynucleotide having a desired property, comprising:
    (a) subjecting a parental polynucleotide to mutagenesis to provide mutants;
    (b) screening the mutants to provide at least two different mutants selected for the desired property as a starting population of polynucleotides;
    (c) subjecting the starting population of polynucleotides comprising the at least two mutants to separate PCR's to result in products of the PCR's:
       (i) a first set of at least two PCR's, which are performed separately from each other, with each PCR using a forward mutation-specific primer which hybridizes to a mutated position in a mutant of the starting population and a reverse universal primer to generates a first common end for the second set of PCR's,
       (ii) a second set of at least two PCR's, which are performed separately from each other, with each PCR using a forward universal primer to generate a second common end for the second set PCR's and a reverse mutation-specific primer which hybridizes to a mutated position in a mutant of the starting population, and
       (iii) optionally a third or more PCR with suitable forward and reverse primers;
    (d) assembling products of the PCR's using a polymerase to obtain said population of variant polynucleotides, wherein the variant polynucleotides differ in at least one position from the parental polynucleotide; and
    (e) optionally amplifying the population of variant polynucleotides.

13. The process of claim 12, wherein the at least one polynucleotide encodes an enzyme.

\* \* \* \* \*

SEQUENCE LISTING

<160> NUMBER OF SEQ ID NOS: 2

<210> SEQ ID NO 1
<211> LENGTH: 945
<212> TYPE: DNA
<213> ORGANISM: Ochrobactrum anthropi
<220> FEATURE:
<221> NAME/KEY: CDS
<222> LOCATION: (1)..(945)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | tgc | aat | aat | tgc | cat | tac | acc | att | cac | ggc | cgg | cat | cat | cat | ttc | 48 |
| Met | Cys | Asn | Asn | Cys | His | Tyr | Thr | Ile | His | Gly | Arg | His | His | His | Phe | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | tgg | gac | aac | tcg | ttc | cag | ccg | gct | gaa | acg | gtc | gcg | ccc | ggc | tcg | 96 |
| Gly | Trp | Asp | Asn | Ser | Phe | Gln | Pro | Ala | Glu | Thr | Val | Ala | Pro | Gly | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | ctg | aaa | ttc | gaa | tgt | ctg | gac | agc | ggc | gca | ggc | cac | tat | cat | cgc | 144 |
| Thr | Leu | Lys | Phe | Glu | Cys | Leu | Asp | Ser | Gly | Ala | Gly | His | Tyr | His | Arg | |
| | | | 35 | | | | | 40 | | | | | 45 | | | |

| | | | | | | | | | | | | | | | | |
|---|---|---|---|---|---|---|---|---|---|---|---|---|---|---|---|---|
| ggc | agc | aca | gtc | gcc | gat | gtg | tcg | acg | atg | gat | ttt | tcc | aag | gtc | aat | 192 |
| Gly | Ser | Thr | Val | Ala | Asp | Val | Ser | Thr | Met | Asp | Phe | Ser | Lys | Val | Asn | |
| | 50 | | | | | 55 | | | | | 60 | | | | | |

| | | | | | | | | | | | | | | | | |
|---|---|---|---|---|---|---|---|---|---|---|---|---|---|---|---|---|
| ccg | gtt | acc | ggc | ccc | atc | ttc | gtc | gat | gga | gcc | aaa | ccg | ggc | gat | gtc | 240 |
| Pro | Val | Thr | Gly | Pro | Ile | Phe | Val | Asp | Gly | Ala | Lys | Pro | Gly | Asp | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | aaa | atc | acc | atc | cac | cag | ttc | gag | cca | tca | ggc | ttc | ggc | tgg | acg | 288 |
| Leu | Lys | Ile | Thr | Ile | His | Gln | Phe | Glu | Pro | Ser | Gly | Phe | Gly | Trp | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aat | att | ccg | ggc | ttc | ggt | ctt | ctc | gcc | gac | gac | ttc | aag | gaa | ccg | 336 |
| Ala | Asn | Ile | Pro | Gly | Phe | Gly | Leu | Leu | Ala | Asp | Asp | Phe | Lys | Glu | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| gcg | cta | gca | ttg | tgg | aac | tac | aat | ccc | aca | acg | ctg | gag | cca | gca | ctc | 384 |
| Ala | Leu | Ala | Leu | Trp | Asn | Tyr | Asn | Pro | Thr | Thr | Leu | Glu | Pro | Ala | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| ttc | gga | gag | cgt | gcg | cgc | gtg | ccg | ctg | aag | ccg | ttc | gcc | gga | acc | atc | 432 |
| Phe | Gly | Glu | Arg | Ala | Arg | Val | Pro | Leu | Lys | Pro | Phe | Ala | Gly | Thr | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| ggc | gtc | gca | ccg | gcg | gaa | aag | ggc | ctg | cat | tcg | gtc | gta | cca | ccg | cgt | 480 |
| Gly | Val | Ala | Pro | Ala | Glu | Lys | Gly | Leu | His | Ser | Val | Val | Pro | Pro | Arg | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cgt | gtc | ggc | ggc | aat | ctc | gac | atc | cgc | gat | ctt | gca | gcc | gga | acc | acg | 528 |
| Arg | Val | Gly | Gly | Asn | Leu | Asp | Ile | Arg | Asp | Leu | Ala | Ala | Gly | Thr | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| ctt | tat | ctg | ccg | atc | gaa | gtc | gaa | ggc | gct | ttg | ttc | tcc | att | ggt | gat | 576 |
| Leu | Tyr | Leu | Pro | Ile | Glu | Val | Glu | Gly | Ala | Leu | Phe | Ser | Ile | Gly | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| acc | cat | gcg | gca | cag | ggc | gac | ggc | gaa | gtg | tgc | ggc | acc | gcc | atc | gaa | 624 |
| Thr | His | Ala | Ala | Gln | Gly | Asp | Gly | Glu | Val | Cys | Gly | Thr | Ala | Ile | Glu | |
| | | 195 | | | | | 200 | | | | | 205 | | | | |

| | | | | | | | | | | | | | | | | |
|---|---|---|---|---|---|---|---|---|---|---|---|---|---|---|---|---|
| agc | gcg | atg | aat | gtc | gct | ctg | acg | ctg | gat | ctc | atc | aag | gat | acg | cca | 672 |
| Ser | Ala | Met | Asn | Val | Ala | Leu | Thr | Leu | Asp | Leu | Ile | Lys | Asp | Thr | Pro | |
| | 210 | | | | | 215 | | | | | 220 | | | | | |

| | | | | | | | | | | | | | | | | |
|---|---|---|---|---|---|---|---|---|---|---|---|---|---|---|---|---|
| ctg | aag | atg | ccc | cgg | ttc | acc | acg | ccg | ggg | cca | gtg | acg | cgg | cac | ctc | 720 |
| Leu | Lys | Met | Pro | Arg | Phe | Thr | Thr | Pro | Gly | Pro | Val | Thr | Arg | His | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gat | acc | aag | ggt | tac | gaa | gtc | acc | acc | ggt | atc | ggg | tcc | gat | ctg | tgg | 768 |
| Asp | Thr | Lys | Gly | Tyr | Glu | Val | Thr | Thr | Gly | Ile | Gly | Ser | Asp | Leu | Trp | |
| | | | | 245 | | | | | 250 | | | | | 255 | | |

```
gaa ggc gcg aaa gcc gcc ctc tcc aac atg atc gac ctt ctt tgc cag    816
Glu Gly Ala Lys Ala Ala Leu Ser Asn Met Ile Asp Leu Leu Cys Gln
        260                 265                 270 acg cag aac ctc aac ccg gtg gat gcc tat atg ctc tgc tcg gcc tgc    864
Thr Gln Asn Leu Asn Pro Val Asp Ala Tyr Met Leu Cys Ser Ala Cys
            275                 280                 285 ggt gat ctg cgt atc agc gaa atc gtc gat cag ccg aac tgg gtc gta    912
Gly Asp Leu Arg Ile Ser Glu Ile Val Asp Gln Pro Asn Trp Val Val
    290                 295                 300 tcg ttc tac ttc ccg cgt tcc gtt ttc gaa taa                        945
Ser Phe Tyr Phe Pro Arg Ser Val Phe Glu
305                 310

<210> SEQ ID NO 2
<211> LENGTH: 314
<212> TYPE: PRT
<213> ORGANISM: Ochrobactrum anthropi

<400> SEQUENCE: 2

Met Cys Asn Asn Cys His Tyr Thr Ile His Gly Arg His His Phe
1               5                   10                  15

Gly Trp Asp Asn Ser Phe Gln Pro Ala Glu Thr Val Ala Pro Gly Ser
            20                  25                  30

Thr Leu Lys Phe Glu Cys Leu Asp Ser Gly Ala Gly His Tyr His Arg
        35                  40                  45

Gly Ser Thr Val Ala Asp Val Ser Thr Met Asp Phe Ser Lys Val Asn
    50                  55                  60

Pro Val Thr Gly Pro Ile Phe Val Asp Gly Ala Lys Pro Gly Asp Val
65                  70                  75                  80

Leu Lys Ile Thr Ile His Gln Phe Glu Pro Ser Gly Phe Gly Trp Thr
                85                  90                  95

Ala Asn Ile Pro Gly Phe Gly Leu Leu Ala Asp Asp Phe Lys Glu Pro
            100                 105                 110

Ala Leu Ala Leu Trp Asn Tyr Asn Pro Thr Thr Leu Glu Pro Ala Leu
        115                 120                 125

Phe Gly Glu Arg Ala Arg Val Pro Leu Lys Pro Phe Ala Gly Thr Ile
    130                 135                 140

Gly Val Ala Pro Ala Glu Lys Gly Leu His Ser Val Val Pro Pro Arg
145                 150                 155                 160

Arg Val Gly Gly Asn Leu Asp Ile Arg Asp Leu Ala Ala Gly Thr Thr
                165                 170                 175

Leu Tyr Leu Pro Ile Glu Val Glu Gly Ala Leu Phe Ser Ile Gly Asp
            180                 185                 190

Thr His Ala Ala Gln Gly Asp Gly Glu Val Cys Gly Thr Ala Ile Glu
        195                 200                 205

Ser Ala Met Asn Val Ala Leu Thr Leu Asp Leu Ile Lys Asp Thr Pro
    210                 215                 220

Leu Lys Met Pro Arg Phe Thr Thr Pro Gly Pro Val Thr Arg His Leu
225                 230                 235                 240

Asp Thr Lys Gly Tyr Glu Val Thr Thr Gly Ile Gly Ser Asp Leu Trp
                245                 250                 255

Glu Gly Ala Lys Ala Ala Leu Ser Asn Met Ile Asp Leu Leu Cys Gln
            260                 265                 270

Thr Gln Asn Leu Asn Pro Val Asp Ala Tyr Met Leu Cys Ser Ala Cys
        275                 280                 285
```

```
Gly Asp Leu Arg Ile Ser Glu Ile Val Asp Gln Pro Asn Trp Val Val
    290             295             300
Ser Phe Tyr Phe Pro Arg Ser Val Phe Glu
305                 310
```